United States Patent
Swarts et al.

[11] Patent Number: 5,879,398
[45] Date of Patent: Mar. 9, 1999

[54] ACETABULAR CUP

[75] Inventors: Dale F. Swarts; William L. Rohr, Jr.; Steve T. Lin; Thirumalai Devanathan; Steven L. Krebs, all of Warsaw; Paul D. Schoenle, South Bend, all of Ind.

[73] Assignee: Zimmer, Inc.

[21] Appl. No.: 388,089

[22] Filed: Feb. 14, 1995

[51] Int. Cl.⁶ .................................................. A61F 2/34
[52] U.S. Cl. ................................................. 623/22; 623/18
[58] Field of Search ................................. 623/22, 16, 18

[56] References Cited

U.S. PATENT DOCUMENTS

| | | | |
|---|---|---|---|
| 4,479,271 | 10/1984 | Bolesky et al. | 623/20 |
| 4,563,778 | 1/1986 | Roche et al. | 623/22 |
| 4,685,923 | 8/1987 | Mathys | 623/22 |
| 4,769,041 | 9/1988 | Morscher | 623/20 |
| 4,813,960 | 3/1989 | Muller | 623/22 |
| 4,883,492 | 11/1989 | Frey et al. | 623/20 |
| 4,923,473 | 5/1990 | Griss et al. | 623/22 |
| 4,969,910 | 11/1990 | Frey et al. | 623/22 |
| 4,978,355 | 12/1990 | Frey et al. | 623/16 |
| 5,171,287 | 12/1992 | Willert et al. | 623/22 |
| 5,236,457 | 8/1993 | Devanathan | 623/16 |
| 5,336,265 | 8/1994 | Serbousek et al. | 623/18 |
| 5,370,698 | 12/1994 | Heimke et al. | 623/22 |

FOREIGN PATENT DOCUMENTS

| | | | |
|---|---|---|---|
| 2639218 | 5/1990 | France | 623/22 |
| 2685192 | 6/1993 | France | 623/22 |
| 2698782 | 6/1994 | France | 623/22 |
| 3130732 | 5/1983 | Germany | 623/22 |

*Primary Examiner*—Mickey Yu
*Assistant Examiner*—Bruce E. Snow
*Attorney, Agent, or Firm*—Todd A. Dawson

[57] ABSTRACT

The present invention is directed to an acetabular cup prosthesis for implantation into a pelvic bone. A cup having a cavity for receiving a femoral head is formed of a polymeric material having a predetermined tensile strength. A backing is disposed about and attached to the polymeric cup. The backing has a porous construction defining interstitial pores, with the pores being sized to receive a portion of the polymeric cup therein and adapted for allowing ingrowth of the bone therein. The portion of the polymeric cup received within the pores results in an interface strength between the polymeric cup and the backing which is substantially equal to the tensile strength of the polymeric material.

1 Claim, 2 Drawing Sheets

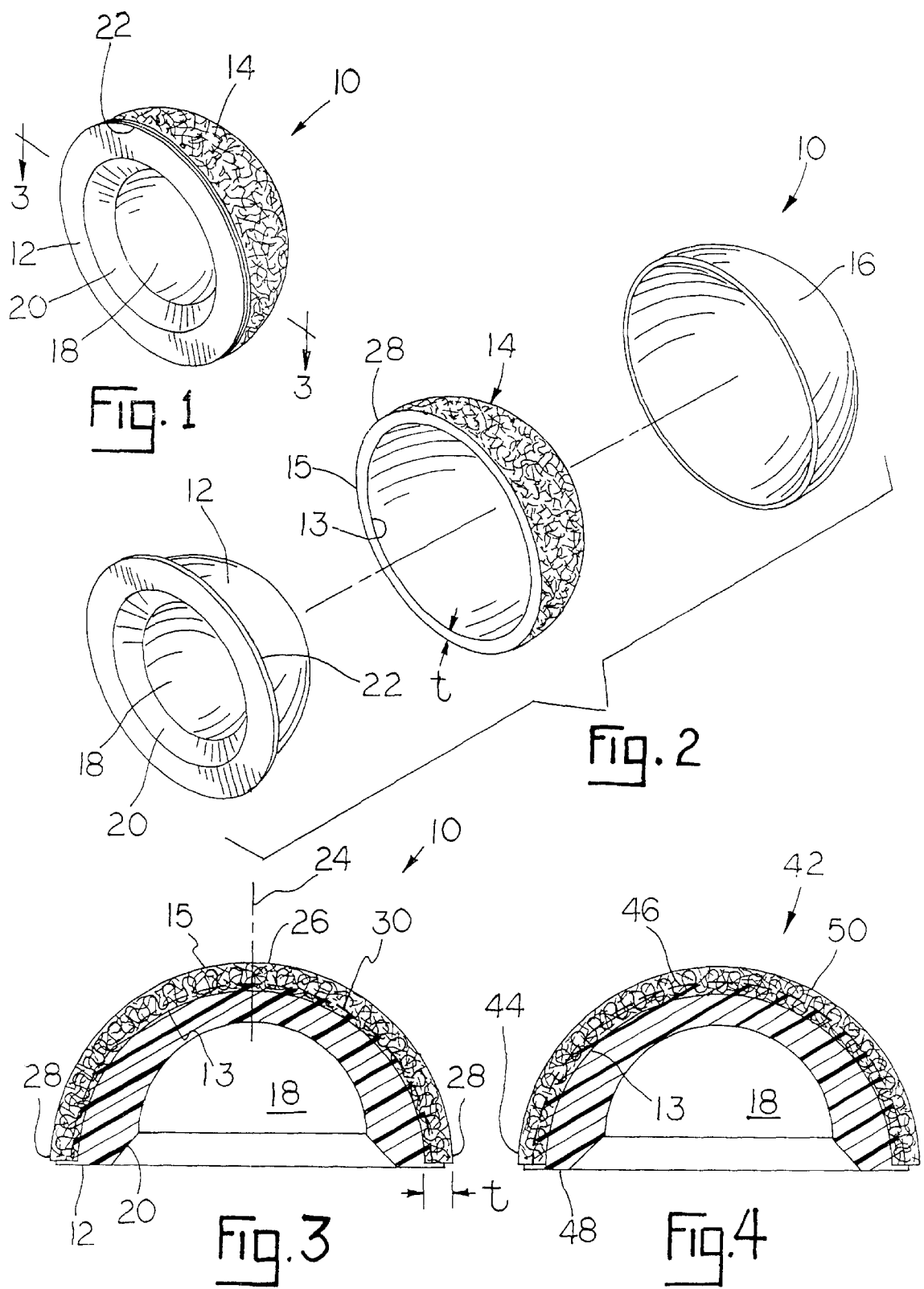

ACETABULAR CUP

BACKGROUND OF THE INVENTION

1. Field of the Invention

The present invention relates to an acetabular cup prosthesis, and, more particularly, to a metal-backed, polymeric acetabular cup prosthesis.

2. Description of the Related Art

It is known to provide an acetabular cup prosthesis having a plastic cup with a metal backing. The metal backing may be in the form of a woven metal grid which is sized to allow bone tissue to grow therein.

With known acetabular cup prostheses, the outside diameter of the cup may vary depending on the size of the pelvic bone of the patient into which the acetabular cup prosthesis is to be implanted. Changing the outside diameter of the acetabular cup in turn changes the radial stiffness of the cup. A radial stiffness which is not stiff enough may hasten deterioration of the polymeric cup and cause pinching of the femoral head, while a radial stiffness which is too stiff may not allow proper loading and stimulation of the bone tissue to encourage ingrowth of the bone into the metal backing.

What is needed in the art is an acetabular cup which may be constructed to substantially conform to a normalized radial stiffness, regardless of the outside diameter of the cup.

What is further needed in the art is an acetabular cup which ensures an adequate attachment between the polymeric cup and metal backing.

SUMMARY OF THE INVENTION

The present invention provides an acetabular cup having a polymeric cup with a metal backing, wherein the interface strength between the polymeric cup and metal backing is substantially equal to the tensile strength of the material from which the polymeric cup is formed. The penetration depth of the polymeric cup into the metal backing, and/or the thickness of the metal backing can be varied according to predetermined design criteria.

The invention comprises, in one form thereof, an acetabular cup prosthesis for implantation into a pelvic bone. A cup having a cavity for receiving a femoral head is formed of a polymeric material having a predetermined tensile strength. A backing is disposed about and attached to the polymeric cup. The backing has a porous construction defining interstitial pores, with the pores being sized to receive a portion of the polymeric cup therein and adapted for allowing ingrowth of the bone therein. The portion of the polymeric cup received within the pores creates an interface strength between the polymeric cup and the backing which is substantially equal to the tensile strength of the polymeric material.

An advantage of the present invention is that the interface strength between the polymeric cup and the metal backing is approximately equal to the tensile strength of the polymeric material from which the polymeric cup is formed.

Another advantage is that it is possible to have a plurality of acetabular cups with different outside diameters, wherein the plurality of acetabular cups have a normalized radial stiffness.

Yet another advantage is that it is possible to have an acetabular cup which has a radial stiffness which is greater at the rim than at the pole portion.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a perspective view of one embodiment of an acetabular cup of the present invention;

FIG. 2 is an exploded, perspective view of the acetabular cup of FIG. 1, and further including a perspective view of a shell;

FIG. 3 is a sectional view of the acetabular cup of FIG. 1, taken along line 3—3:

FIG. 4 is a sectional view of another embodiment of the acetabular cup of the present invention, having a different predetermined penetration depth;

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 5:
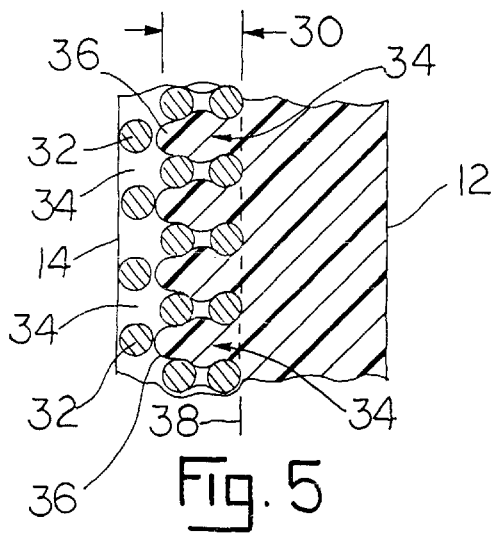
FIG. 5 is a simplified fragmentary, sectional view illustrating penetration of the polymeric cup into the porous metal backing.

Referring now to the drawings and more particularly to FIGS. 1–3, there is shown an acetabular cup 10 of the present invention, which generally includes a polymeric cup 12, metal backing 14 and shell 16. Shell 16 is constructed of a filler material which temporarily occupies a predetermined cross-sectional thickness of metal backing 14 during the manufacturing process, as will be described hereinafter. Shell 16 can be constructed, e.g., of an amorphous polymer such as polysulfone, polyethersulfone, polycarbonate, polyetherimide, or polymethylmethacrylate.

Polymeric cup 12 includes a cavity 18 for receiving a femoral head. Beveled edge 20 allows proper articulation of the femoral head within cavity 18. An outer peripheral flange 22 overlies a portion of metal backing 14 and extends toward the outside diameter of the rim of metal backing 14. Polymeric cup 12 is formed of a polymeric material having a relatively low friction coefficient and suitable wear characteristics, such as high density polyethylene (HPD) or ultra-high-molecular weight polyethylene (UHMWP). In the embodiment shown in the drawings, polymeric cup 12 is formed of a linear UHMWP having a molecular weight of between 1 to 8 million.

Metal backing 14 is attached to polymeric cup 12 and has a thickness "t" extending between a radially inner portion 13 and radially outer portion 15. Metal backing 14 is substantially axisymmetric about an axis 24 at a pole portion 26, and has a maximum outside diameter at a rim 28. In the embodiment shown, metal backing 14 is constructed of fiber metal which is sintered together. The metal fibers occupy about 50 percent of the volume of metal backing 14, with the remaining volume being initially occupied by air. Metal backing 14 is thus of porous construction and the spaces between the metal fibers define interstitial pores of metal backing 14.

In general terms, the manufacture of acetabular cup 10 is as follows: First, porous metal backing 14 is formed using known methods of construction, such as sintering a fiber metal. Backing 14 is placed within shell 16 which is thereafter diffused into metal backing 14 a predetermined thickness. For details of such a process, reference is made to U.S. Pat. No. 5,236,457, which is assigned to the assignee of the present invention and incorporated herein by reference.

Metal backing 14, including shell 16 diffused therein, is placed within a mold and a polymeric material is injected into the mold to define and form polymeric cup 12. Since shell 16 only penetrates a predetermined depth into radially outer portion 15 of metal backing 14, the polymeric material which is injected into the mold also penetrates into radially inner portion 13 of metal backing 14, as indicated by penetration depth 30 (FIG. 3). Shell 16 is then dissolved from metal backing 14 using a suitable solvent, such that a porous surface exists at the radially outer portion of metal backing 14 which is suitable for allowing ingrowth of bone tissue therein.

Figure 6:
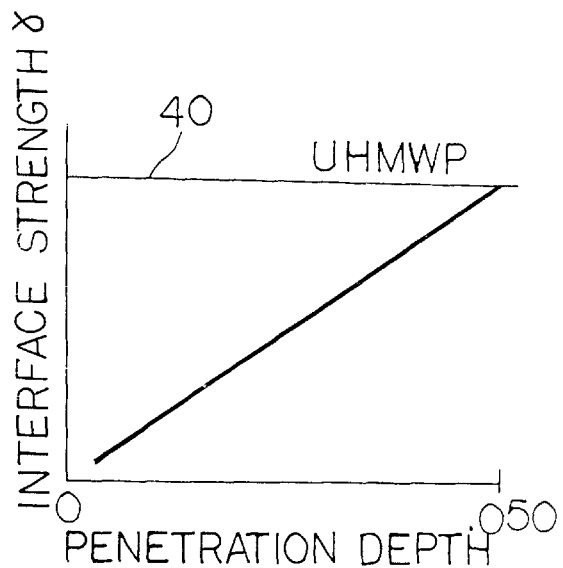
FIG. 6 is a graphical illustration of the relationship between the interface strength of the acetabular cup and the penetration depth of the polymeric cup into the metal backing.
Figure 8:
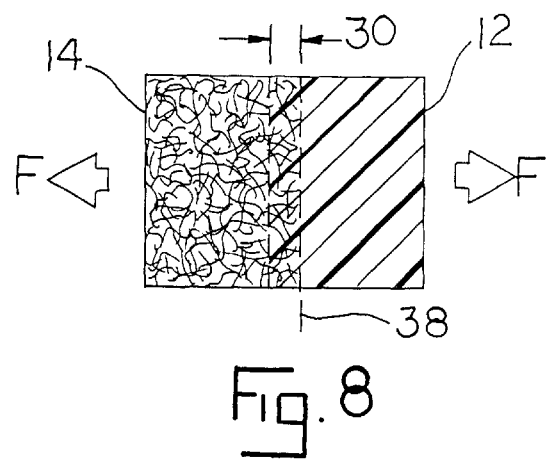
FIG. 8 is a simplified graphical illustration of one method of determining the interface strength between the metal backing and the polymeric cup.

Referring now to FIGS. 5, 6 and 8, the interrelationship between polymeric cup 12 and metal backing 14 will be described in further detail. FIG. 5 is a simplified view illustrating the general concept of the interface strength between polymeric cup 12 and metal backing 14. Broadly speaking, penetration depth 30 must be of sufficient magnitude such that polymeric cup 12 cannot be separated from metal backing 14 without permanent deformation of polymeric cup 12. More particularly, metal backing 14 includes a plurality of metal fibers 32 which are disposed at random orientation, (but which are shown at predetermined and organized orientations in FIG. 5 for ease of illustration). The spaces between metal fibers 32 define interstitial pores 34 which are sized to allow penetration of polymeric cup 12 and bone tissue (not shown). When polymeric cup 12 is molded into metal backing 14, a plurality of fingers 36 are created and penetrate into interstitial pores 34 of metal backing 14. If penetration depth 30 is not of sufficient magnitude and a tensile or separation force is applied between polymeric cup 12 and metal backing 14, fingers 36 will simply be stripped out of interstitial pores 34, resulting in a relatively low interface strength between polymeric cup 12 and metal backing 14.

On the other hand, polymeric cup 12 has an inherent tensile strength associated with the particular material from which polymeric cup 12 is formed. If penetration depth 30 of fingers 36 into interstitial pores 34 is of sufficient magnitude, then fingers 36 will not be stripped from interstitial pores 34 when a separation force is applied generally perpendicular to interface 38. Rather, fingers 36 will tear along interface 38, resulting in permanent deformation of polymeric cup 12. As is known, the tensile strength of fingers 36 is the same as that of the tensile strength of the remainder of polymeric cup 12. Moreover, the tensile strength of a material is a function of the tensile force applied to a material and the area over which the tensile force is applied. The area over which the separation force between polymeric cup 12 and metal backing 14 is applied is not the total area therebetween, but rather is the effective area therebetween or summation of all the cross-sectional areas of fingers 36. For the particular embodiment shown in FIGS. 1–3, and as indicated above, metal backing 14 has a volumetric porosity percentage of about 50 percent. Accordingly, the effective area of metal backing 14 at interface 38 is approximately equal to the total area of metal backing 14 at interface 8, multiplied by 0.50.

Assuming ideal conditions such that penetration depth 30 for each and every finger 36 is sufficiently large, then each finger 36 would tear on application of a separation force between polymeric cup 12 and metal backing 14 at interface 38. However, it is possible that penetration depth 30 is only of a magnitude such that the majority of fingers 36 tear when a separation force is applied, while a much lesser number of fingers 36 are stripped out of interstitial pores 34. Accordingly, the interface strength between polymeric cup 12 and metal backing 14 may be between 70 to 100 percent of the tensile strength of polymeric cup 12. Further, penetration depth 30 and interstitial pore size 34 could be such that for a particular acetabular cup, the interface strength between polymeric cup 12 and metal backing 14 falls within the range of between 70 to 80 percent, 80 to 90 percent and/or 90 to 100 percent of the tensile strength of the material from which polymeric cup 12 is formed.

Referring now to FIG. 6, the interrelationship between the interface strength of polymeric cup 12 and metal backing 14 along interface 38, versus the penetration depth of fingers 36 into metal backing 14 is shown in graphical form. The graphical illustration corresponds to the embodiment of FIGS. 1–3. Horizontal line 40 corresponds to the tensile strength of ultra-high-molecular weight polyethylene from which polymeric cup 12 of FIGS. 1–3 is formed, and is the maximum interface strength possible between polymeric cup 12 and metal backing 14. As indicated, the interface strength between polymeric cup 12 and metal backing 14 increases with a corresponding increased penetration depth, and reaches a maximum value at a penetration depth of about 0.050 inch, corresponding to the tensile strength of UHMWP.

FIG. 8 is a simple block diagram, illustrating a method of determining an interface strength between polymeric cup 12 and metal backing 14. One possible way to determine the interface strength is to cut a small portion or test sample from acetabular cup 10 and attach a suitable device to each of polymeric cup 12 and metal backing 14 for applying a tensile force F in a direction generally perpendicular to interface 38. Tensile force F is increased in magnitude until polymeric cup 12 separates from metal backing 14 along interface 38. The numeric value of the tensile force F required to separate polymeric cup 12 from metal backing 14 is divided by the effective area of metal backing 14 at interface 38. The effective area is calculated by multiplying the cross sectional area of the test sample at interface 38 with the volumetric porosity percentage of metal backing 14, e.g., 50 percent.

FIG. 4 illustrates another embodiment of an acetabular cup 42 of the present invention. Acetabular cup 42 is similar to the embodiment shown in FIG. 3, but has a different outside diameter at rim 44 and also has a different penetration depth 46. Because acetabular cup 42 has a different outside diameter at rim 44, the stiffness of acetabular cup 42 in a radial direction would normally be different than that of acetabular cup 10 shown in FIG. 3. By varying penetration depth 46 of polymeric cup 48 into metal backing 50, it is possible to substantially normalize, i.e., equalize, the stiffness between acetabular cup 10 and acetabular cup 42 in a radial direction. That is, each of acetabular cup 10 and acetabular cup 42 have substantially the same stiffness in a radial direction.

In the embodiment shown in FIG. 4, penetration depth 46 is different from penetration depth 30 shown in FIG. 3 to thereby normalize the stiffnesses between acetabular cup 10 and acetabular cup 42. However, it is to be understood that it is likewise possible to maintain a common penetration depth between acetabular cups having different diameters, and vary the thickness of the metal backing from one cup to another to thereby normalize the radial stiffness.

Figure 7:
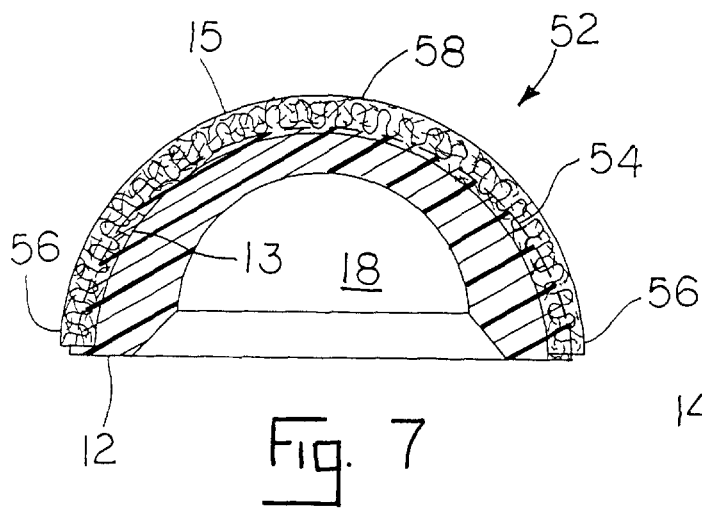
FIG. 7 is a sectional view of another embodiment of the acetabular cup of the present invention, having a penetration depth which is larger at the rim of the backing and lesser at the pole portion of the backing.

Referring now to FIG. 7, another embodiment of an acetabular cup 52 of the present invention is shown. In contrast with the embodiments shown in FIGS. 3 and 4, the embodiment shown in FIG. 7 has a penetration depth 54 which is greater at a rim 56 then at a pole portion 58. In theory, when acetabular cup 52 is press fit into an acetabulum of a pelvic bone, the radially compressive forces exerted against acetabular cup 52 by the pelvic bone are greater at rim 56 than at pole portion 58. By having a greater penetration depth 54 at rim 56 than at pole portion 58, it is possible to construct acetabular cup 52 such that the radial stiffness at rim 56 is greater than the radial stiffness at pole portion 58.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A first and second acetabular cup prosthesis, each of said first and second acetabular cups having a different outside diameter at a rim thereof, each of said first acetabular cup and said second acetabular cup comprising:

a polymeric cup having a cavity for receiving a femoral head; and a backing disposed about and attached to said polymeric cup, said backing having a thickness and further having a porous construction defining interstitial pores, said polymeric cup being attached to said backing by penetrating into said pores a predetermined penetration depth;

at least one of said backing thickness and said penetration depth varying between said first acetabular cup and said second acetabular cup, whereby each of said first acetabular cup and said second acetabular cup have substantially the same stiffness in a radial direction.

* * * * *